United States Patent [19]

House

[11] Patent Number: 5,811,532
[45] Date of Patent: Sep. 22, 1998

[54] COVALENTLY BOUND, POLYSACCHARIDE-BASED CHIRAL STATIONARY PHASES

[75] Inventor: David W. House, Arlington Heights, Ill.

[73] Assignee: UOP LLC, Des Plaines, Ill.

[21] Appl. No.: 884,835

[22] Filed: Jun. 30, 1997

[51] Int. Cl.[6] .......................... C12P 19/26; G01N 33/552; B01J 20/10
[52] U.S. Cl. .......................... 536/18.7; 536/18.7; 536/56; 536/123.1; 210/635; 106/162.1; 106/162.71; 106/205.1
[58] Field of Search ...................................... 536/123.1, 56, 536/18.7; 106/162.1, 162.71, 205.1; 210/635

[56] References Cited

U.S. PATENT DOCUMENTS 4,619,970 10/1986 Okamoto et al. ........................ 525/100
4,861,872 8/1989 Okamoto et al. ....................... 536/18.7

OTHER PUBLICATIONS

Y. Okamoto, *J. Chromatog.*, 666 (1994), 403–19.
Y. Okamoto et al., *J. Liq. Chromatog.*, 10 (1987), 1613–28.

*Primary Examiner*—Gary L. Kunz
*Attorney, Agent, or Firm*—Thomas K. McBride; Frank S. Molinaro

[57] ABSTRACT

There are described stable, non-leaching chiral stationary phases in which a chiral polysaccharide or polysaccharide derivative is covalently bound through a spacer to the surface hydroxyl groups of a refractory inorganic oxide. The spacer molecules are omega-isocyanatoalkylene silanes. Favored refractory inorganic oxides are alumina and silica gel. Cellulose esters and cellulose phenyl carbamates are among the most favored of the chiral polysaccharides.

26 Claims, No Drawings

COVALENTLY BOUND, POLYSACCHARIDE-BASED CHIRAL STATIONARY PHASES

BACKGROUND OF THE INVENTION

Ever since Pasteur discovered the property of optical activity displayed by chiral compounds, the resolution of racemic mixtures into their enantiomeric components has posed a challenge. Substantial progress in separating enantiomeric pairs has been achieved since Pasteur's laborious hand separation of the enantiomeric crystals of racemic sodium ammonium tartrate, yet methods of resolution, and the materials used therefor, remain a formidable obstacle to commercial production of optically active organic substances.

A traditional method of resolution comprises reacting a racemic mixture with a second optically active substance to form a pair of diastereomeric derivatives. Such derivatives generally have different physical properties which permit their separation by conventional means. For example, fractional crystallization often permits substantial separation to afford at least one of the diastereomers in a pure state, or largely so. An appropriate chemical transformation then converts the purified derivative, which was formed initially solely to prepare a diastereomeric pair, into one enantiomer of the originally racemic compound. This traditional method is exemplified by the reaction of naturally occurring optically active alkaloids, for example, brucine, with racemic acids to form diastereomeric salts, with release of an optically active organic acid from a purified diastereomer upon acidification of the latter.

Such traditional methods suffer from many limitations. Generally, only one of the enantiomeric pairs can be obtained, so yields are necessarily less than 50%. The separation of the material so obtained usually is incomplete, leading to materials with enhanced rather than complete optical purity. The optically active materials used to form the diastereomers frequently are expensive and quite toxic—the alkaloids as a class are good examples—and are only partially recoverable. Regeneration of optically active material from its derivative may itself cause racemization of the desired compound, leading to diminution of optical purity. For example if optically active benzyl alcohols are prepared through their diastereomeric ester derivatives, subsequent acid hydrolysis of the latter to regenerate the alcohol may be accompanied by appreciable racemization.

With the advent of chromatography diverse variations on the basic theme of separating diastereomers became possible. These approaches undeniably represent substantial advances in the art, yet fail to surmount the basic need, and associated problems, to prepare diastereomeric derivatives of the desired compound and to transform such derivatives after separation to the optically active compounds of interest.

Chromatographic methods of separating diastereomers offer advantages of general application, mild conditions which generally preclude chemical or physical transformation, efficiency of recovery and separation which are limited only by the number of theoretical plates employed and the capability of utilization from a milligram to kilogram scale. Translation from a laboratory to industrial scale has proved feasible, and commercial processes employing chromatographic separation occupy an important position in the arsenal of available industrial methods. For such reasons, methods based on chromatographic separation remain under intensive exploration.

To circumvent the disadvantage of separating diastereomeric derivatives of a compound while retaining the advantage of chromatographic separation, recent advances in the art have employed chiral, optically active compounds in association with the chromatographic support. The theory underlying this approach is that chiral material will have differential weak interactions with enantiomers, for example, hydrogen bonding, or acid-base interactions generally. Such weak interactions lead to reversible formation of entities which we refer to as complexes, and the equilibrium constant characterizing complex formation will be different for each member of the enantiomeric pair. The different equilibrium constants manifest themselves as a differing partition coefficient among the phases in a chromatographic process, leading ultimately to separation of enantiomers.

Thus, enantiomers of some chromium complexes were resolved by chromatography on powdered quartz, a naturally occurring chiral material. Karagounis and Coumolos, *Nature*, 142, 162 (1938). Lactose, another naturally occurring chiral material, was used to separate p-phenylene-bis-iminocamphor. Henderson and Rule, *Nature*, 141, 917 (1938). However, despite this knowledge substantiating theoretical considerations, advances in the art have been tortuous at best.

A major obstacle has been development of a chiral solid phase capable of resolving, at least in principle, a broad class of racemic organic compounds, with a stability which permits repeated usage, and with adequate capacity to make separation feasible on a preparative scale. Gil-Av has made a major contribution toward one kind of solution by gas-liquid phase chromatographic resolution of enantiomers using columns coated with N-trifluoroacetyl derivatives of amino acids, di-and tri-peptides. Gil-Av and Nurok, "Advances in Chromatography", Volume 10, Marcel Dekker (New York), 1974. However, the advances suffer practical limitations originating from the need to have volatile substrates and the inability to scale up the methods employed.

Another advance is represented by the work of Baczuk and coworkers, *J. Chromatogr.*, 60, 351 (1971), who covalently bonded an optically active amino acid through a cyanuric acid linkage to a modified dextran support and utilized the resulting material in column chromatography to resolve 3,4-dihydroxyphenylalanine. A different approach is exemplified by polymerization of optically active amides with the resulting polymer used as a solid phase in liquid-solid chromatography. Blaschke and Schwanghart, *Chemische Berichte*, 109, 1967 (1976).

More recently it has become an accepted reality that enantiomeric medicinals may have radically different pharmacological activity. For example, the (R)-isomer of propranolol is a contraceptive whereas the (S)-isomer is a beta-blocker. An even more dramatic and tragic difference is furnished by thalidomide where the (R)-enantiomer is a safe and effective sedative when prescribed for the control of morning sickness during pregnancy whereas the (S)-enantiomer was discovered to be a potent teratogen leaving in its wake a multitude of infants deformed at birth. This has, in part, provided the motivation for developing additional tools for chiral separations. Chromatographic processes, especially liquid chromatography, appear to offer the best prospects for chiral separations. One variant of the latter utilizes a chiral eluents in combination with chiral stationary phases, which has the critical aspect that a variety of chiral stationary phases be available to the practitioner. In recent years substantial progress has been made by developing a class of chiral stationary phases based upon derivatized polysaccharides, especially cellulose, adsorbed on a carrier such as silica gel or a modified silica gel. This recently has been summarized by Y. Okamoto, *J Chromatog.*, 666 (1994), 403-19.

One limitation of the prior art polysaccharide chiral stationary phases is that the chiral component is merely adsorbed on the carrier which has the unavoidable consequence that the stationary phase itself may leach with appropriate solvents. The practical consequence of a chiral stationary phase bound solely by adsorption is to limit the range of solvents which may be used as eluents in the chromatographic resolution of racemates. This is an undesirable restriction which limits not only the flexibility of chromatography-based optical resolution but also substantially increases its cost through the gradual loss of expensive chiral stationary phase.

The need for a more "permanent" chiral stationary phase has been recognized and solutions for polysaccharide-based systems designed on a covalent tether anchoring the chiral stationary phase to the carrier have been disclosed. Y. Okamoto et al., *J. Liq. Chromatog.*, 10 (1987), 1613-28; U.S. Pat. No. 4,619,970. The foregoing unquestionably recognizes the underlying problem and provides a rational approach to its solution, yet it is only a first step which itself possesses significant limitations. In particular, the "tether" holding the chiral stationary phase to the carrier is relatively long and implementing the tether requires an undesirable number of process steps. Consequently, we embarked on a program where the chiral stationary phase is covalently bound to a carrier more directly and with fewer requisite process steps. Our solution, described in detail within, is rather general in scope for polysaccharide-based chiral stationary phases, both as regards the method of preparing the product and the structure of the resulting chiral stationary phase.

In particular, the tether—more commonly referred to as a "spacer"—is an alkylene group covalently bonded at one terminus to the carrier via a —O—Si linkage and covalently bonded at its second terminus to the polysaccharide via a urethane linkage, NHC(O)O—. Both covalent links are chemically stable to a broad range of pH, are resistant to thermal degradation, and form covalent links to a suitable range of carriers and to polysaccharides generally. The resulting covalently bound polysaccharides and derivatized polysaccharides, including celluloses, show chiral recognition toward a wide range of substrates, are readily prepared and modified, and manifest excellent resolving power with respect to racemates. The covalently bonded chiral stationary phases are very easily prepared, utilizing an entity with "dual agency," i.e., the same agent acts as both a silane treating agent (i.e., reacts with the free hydroxyl groups of the carrier) and a polysaccharide binder. This is in stark and significant contrast to the teachings of Okamoto, U.S. Pat. No. 4,619,970, which requires two different and distinct agents, one acting as a silane treating agent and the other as a polysaccharide binder, with the added proviso that the two agents also be capable of reacting with each other. Our simplified approach is procedurally more efficient, more cost effective, and affords chiral stationary phases with more favorable properties than those of the prior art.

Covalently attaching the derivatized polysaccharide to a solid support virtually eliminates leaching, regardless of the mobile phase. This permits the use of many more types of mobile phases, as well as permitting switching from forward to reverse phase eluents using the same column without fear of destroying the chiral support due to leaching or plugging of the column. This benefit makes the derivatized polysaccharide-based chiral supports much more effective for traditional single pass chromatography, for recycle-type chromatography, for simulated moving bed-based chromatography, and simple preferential adsorption of one enantiomer over the other.

SUMMARY OF THE INVENTION

The purpose of our invention is to provide chiral stationary phases capable of a broad range of chiral recognition and which are covalently bonded to a refractory inorganic oxide as a carrier so as to essentially eliminate leaching of the chiral component and permit the stationary phase to be employed over a quite broad range of solvents. An embodiment comprises as the chiral stationary phase a carrier covalently bonded to one terminus of an isocyanato alkylene siloxane as a spacer whose other terminus is covalently bonded to a chiral polysaccharide or derivatized polysaccharide. In a more specific embodiment the refractory inorganic oxide has bound surface hydroxyl groups and is silica or alumina. In yet another specific embodiment the spacer is a 3-isocyanatopropyl silane. In yet another specific embodiment the polysaccharide is cellulose. In a still more specific embodiment the polysaccharide is a cellulose urethane. Other embodiments and aspects will be apparent from the ensuing discussions.

DESCRIPTION OF THE INVENTION

The problem is to prepare a chiral stationary phase which manifests broad chiral recognition, which can be readily modified to tailor the chiral recognition to a particular task, which is resistant to leaching using the entire spectrum of solvents normally employed in liquid chromatography, which is thermally stable, and which is unreactive to most types of substrates likely to be separated. Our solution to this problem is to covalently bind a chiral polysaccharide or derivatized polysaccharide to a spacer molecule whose other end is covalently bonded to the bound surface hydroxyl groups of a refractory inorganic oxide. The resulting chiral stationary phase is quite stable, is essentially non-leaching, and because the polysaccharide or polysaccharide derivative can be modified broadly one has available a vast number of chiral recognition sites in a stable chiral stationary phase. Our products are conceptually quite simple and ultimately consist of a carrier, a spacer molecule, and a chiral polysaccharide or derivatized polysaccharide. What is important is how the foregoing components are brought together to afford the resulting chiral stationary phase. The procedures for preparing the products of our invention also are relatively simple, efficient, and inexpensive.

The carriers of our invention are refractory inorganic oxides which generally have a surface area of at least about 35 $m^2/g$, preferably greater than about 50 $m^2/g$, and more desirably greater than 100 $m^2/g$. There appears to be some advantage to working with materials having as high a surface area as possible, although exceptions are known which preclude making this a general statement. Suitable refractory inorganic oxides include alumina, titania, zirconia, chromia, silica, boria, silica-alumina, and combinations thereof. Of these silica is particularly preferred.

It is required that the refractory inorganic oxide has bound surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Since the presence of merely adsorbed water is generally detrimental to the preparation of the chiral stationary phases of our invention, the refractory inorganic oxides are first treated to remove surface hydroxyl groups arising from water, most usually by heating at a temperature which specifically and preferentially removes physically adsorbed water without chemically altering the other hydroxyl groups. Where the inorganic oxide is silica, for example, temperatures up to about 120° C. are usually satisfactory. For alumina, temperatures in the range 125°–700° C. have proved adequate, and we prefer 125°–250° C. As an alternative to heat treatment, silica gel may be activated by azeotropically removing the adsorbed water using benzene, toluene, or another solvent forming an azeotrope with water.

The reason for the requirement that the carrier have bound surface hydroxyl groups is that these hydroxyl groups form one end of a tether which results from reaction of the bound surface hydroxyl groups with a silane functionality on a spacer molecule with formation of a covalent O-Si bond as part of the structure carrier-O-Si-spacer.

The spacer molecules of our invention have the formula $(RO)_x SiHal_y(CH_2)_n$-NCO, i.e., isocyanato alkylene silanes. The silane part of our spacer molecules contain either halogen or alkoxy groups, either alone or in combination. Chlorine is by far the most common halogen which may be used in the practice of our invention, although bromine also can be used equally well. As for the alkyl group of RO, R may be any alkyl group, but preferably is a lower alkyl having from 1 through about 6 carbon atoms, with C1 and C2 alkyl groups particularly desirable. The silicon atom is separated from the isocyanato group by a chain of methylene groups, $CH_2$. The length of this chain is given by n which is an integer between 2 and about 12, with n=from 2 to 4 especially desirable. The subscripts x and y also are integers where their sum is equal to 3.

The other terminus of the spacer molecule is covalently bonded through the isocyanato group to an hydroxyl group of a chiral polysaccharide, whether synthetic, natural, or modified, via formation of a urethane linkage. Cellulose and cellulose derivatives are by far the most preferred polysaccharides used in the practice of this invention. However, other polysaccharides which may be successfully utilized, either per se or via suitable derivatives, include amylose, amylopectin, dextran, inulin, levan, chitin, pullulan, agarose and starch. Although the polysaccharides have been characterized above as the final polysaccharide, they can be equally well characterized by the type of monomeric structural unit which is present in the oligomeric or polymeric product. So, for example, amylose consists of alpha-1,4-glucan subunits. Accordingly, the monomeric saccharide subunits in the polysaccharides of our invention include alpha-1,4-glucan, alpha-1,6-glucan, beta-1,6-glucan, beta-1,3-glucan, alpha-1,3-glucan, beta-1,2-glucan, beta-1,4-galactan, beta-1,4-mannan, alpha-1,6-mannan, beta-1,2-fructan, beta-2,6-fructan, beta-1,4-xylan, beta-1,3-xylan, beta-1,4-chitosan, beta-1,4-N-acetylchitosan, and so forth.

The covalently bound chiral polysaccharides themselves have utility as resolving agents, but their derivatives have been more commonly used because of their distinctly better capabilities of resolving racemic mixtures. Thus, polysaccharide esters and carbamates have been found particularly useful as chiral stationary phases, and a multitude of derivatives manifesting chiral recognition have been taught by Okamoto in, e.g., U.S. Pat. No. 4,861,872 and J. Chromatog., A, 666 (1994), 403–419, all of which is hereby included by reference. We have observed that the 3,5-dimethylphenylcarbamate derivative of cellulose is a particularly desirable polysaccharide to be covalently bonded via the spacer molecule to the carriers of our invention.

In principle, the chiral stationary phases of our invention may be made in two distinctly different ways. One method is to first silanize the carrier, i.e., treat the carrier with the spacer agents of our invention in order to covalently bond the carrier to the spacer agent via -O-Si bonds. The silanized carrier then can be reacted with a polysaccharide via the isocyanato group of the covalently bonded spacer in order to form the chiral stationary phase. This procedure also has two variants in the case where a derivatized polysaccharide is used: in one variant the polysaccharide could be reacted with the isocyanate and thereafter reacted with the derivatizing agent; the other variant is one where the polysaccharide is first derivatized, and the derivatized polysaccharide having some free hydroxyl groups is subsequently reacted with the isocyanate group of the spacer. This approach may be summarized symbolically as follows.

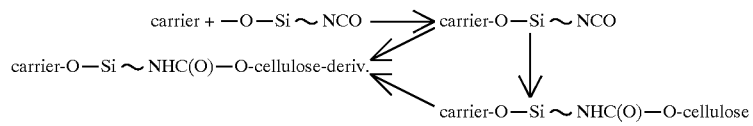

The other procedure is to first react the isocyanate group of the spacer with the polysaccharide, and subsequently reacting that with the carrier.

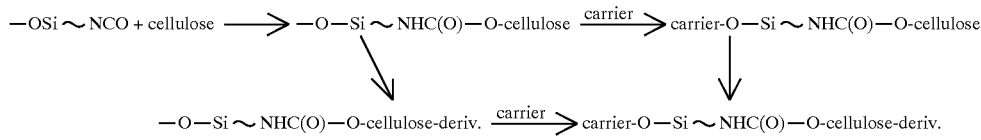

This procedure also has at least two subvariants: one where the polysaccharide is derivatized prior to silylation of the carrier, the other where the polysaccharide is derivatized after silylation of the carrier. The procedure we favor is to first react the spacer molecule with the polysaccharide, silylate the carrier with the derivatized bound cellulose, and thereafter derivatize the free hydroxyls of the bound polysaccharide with an excess of the derivatizing agent. The reason for our favoring this procedure is that it appears to afford the fewest number of side products which otherwise are difficult to remove. However, it is to be clearly understood that the procedure is a matter of choice and that the final chiral stationary phase which is formed is not substantially influenced by the particular procedure which is used in its formation.

Describing our preferred procedure in greater detail, a chiral polysaccharide is reacted with the isocyanatosilane to form a urethane linkage between the polysaccharide and spacer molecule. An amount of spacer is used which is between about 0.05 and about 0.2 moles relative to the subunits of the polysaccharide. That is, the number of spacer molecules is between about 5 percent and 20 percent of the number of sugar subunits in the polysaccharide. It is found that it is most desirable if only a fraction of the subunits bear a spacer molecule, and it is most preferred that only about 10 mole percent of the spacer relative to the sugar subunits be employed. Although a larger percentage of spacer molecules may be used in the practice of our invention no advantage generally accrues therefrom.

The polysaccharide to which is attached the spacer molecule via urethane linkages bears a silane group at the other spacer terminus which is reactive with the bound hydroxyl groups of the carrier. In our preferred procedure this is then reacted with the carrier, most simply by refluxing a slurry of the spacer molecule-polysaccharide product and the carrier in benzene or toluene. Periodically, some of the solvent is allowed to distill from the slurry to help drive the reaction between the spacer molecule-polysaccharide product and the carrier to completion. Fresh solvent is then added to replace that which was distilled. The resulting material, which can be represented symbolically as carrier-O-Si-NHC(O)O-polysaccharide, is then either used per se as a chiral stationary phase, but most usually is derivatized, in a manner well known to the skilled artisan, by reacting between about 70 and 100% of the available hydroxyl groups of the bound polysaccharide with a suitable derivatizing agent, such as an organic isocyanate, e.g., 3,5-dimethylphenyl isocyanate. Since the process of derivatization is so well known no further description will be given here.

The following examples are merely exemplary of our invention and are not intended to limit it in any way. Variants will be readily appreciated by the skilled artisan, and it is intended that these variants be subsumed within our invention as claimed.

EXAMPLES

Liquid Chromatography System

The HPLC system was composed of the following: a Spectra-Physics SpectraSYSTEM P1500 pump capable of flow rates up 10 mL/min, a Rheodyne 7125 sample injector equipped with a 5 $\mu$L loop, a Waters Associates Model 440 dual wavelength absorbance detector monitoring at 254 and 280 nm, a Waters 410 Differential Refractometer, and a Thermo Separation Products ChromJet recording integrator. All tubing used was stainless steel 1/16 inch O.D. by 0.009 inch I.D. tubing.

The void volume ($t_0$) of each column was determined using an unretained sample (toluene or 1,3,5-tri-t-butylbenzene). Separation values ($\alpha$) were determined according to the formula: $\alpha=(t_2-t_0)/(t_1-t_0)$. k-Values were determined using the formula: $k'x=(t_x-t_0)/t_0$.

Synthesis of Cellulose-3,5-Dimethylphenylcarbamate-carbamoylpropyltriethoxysilane Covalently Bound to Silica Gel To a 100 mL, three-necked, round-bottomed flask equipped with a reflux condenser, a thermometer (attached to a Therm-o-watch temperature controller), a Teflon-coated stirring bar, and a heating mantle, were added 1.52 g (9.371 mmol) of microcrystalline cellulose (unit FW=162.16; J. T. Baker) and 40 mL of dry pyridine (Aldrich Chemical Company). To the top of the condenser were attached a 10 mL equilibrated dropping funnel and a nitrogen line. To the dropping funnel were added 0.24 g (0.9371 mmol) of 3-isocyanatopropyltriethoxysilane (Huls America) dissolved in about 10 mL of dry pyridine. The flask contents were stirred, heated to 100° C., and the isocyanate slowly added over a two hour period. The progress of the reaction was followed by FT-IR.

The reaction was allowed to continue for an additional 22 hours; whereupon, the pyridine was stripped from the reaction mixture using a stream of dry nitrogen, and the reaction temperature lowered to below 60° C. Pyridine also may be removed by evaporation at reduced pressure. The dropping funnel was removed from the condenser and a Dean-Stark trap was added between the flask and the condenser. The nitrogen line was attached to the top of the condenser. To the product were added 60 mL of dry chloroform followed by 5.00 g of Adsorbosphere 5$\mu$ silica gel (Alltech Associates, Inc.). The slurry was gently stirred and the reaction mixture brought to reflux. Periodically, about 20 mL of chloroform were removed from the trap and replaced with fresh, dry chloroform. After two hours, the chloroform was replaced with dry benzene and refluxing was continued for about 16 hours. Periodically over this time period, about 20 mL of benzene were removed from the trap and replaced with fresh, dry benzene.

At the end of 16 hours, the reaction was stopped and the reaction slurry was cooled then filtered on a sintered glass funnel. The filter cake was washed sequentially (3×30 mL) with benzene, acetone, methanol, acetone, and pentane. The silica gel was dried in a vacuum oven at 5 torr for 2.5 hours at about 60° C. to yield 6.40 g of white powder.

The white powder from above (6.23 g) was added to the same reaction apparatus as before along with 30 mL of dry toluene. The reaction temperature was brought up to 90° C. and 5.00 g of 3,5-dimethylphenylisocyanate dissolved in about 10 g of dry pyridine were slowly added over 1.5 hours via a dropping funnel attached to the top of the condenser. After 24 hours, the reaction was stopped and the slurry filtered on a sintered glass funnel. The filter cake was washed sequentially (3×30 mL) with toluene, acetone, methanol, acetone, and pentane then air dried. The modified silica gel was placed in a Soxhlet extractor and extracted for 8 hours with THF, then dried in a vacuum oven at 5 torr for 5 hours at about 60° C. to yield 7.28 g of white powder. Chemical analysis: C, 25.4; H, 2.36; N, 2.08. This material is identified below as A.

Enantiomeric Resolution Using Chiral Stationary Phases

Separations effected by CSP "A" prepared above were compared with those obtained using commercially available CSPs. In all cases the eluent was 10% isopropyl alcohol in hexane flowing at 1.0 mL/min. A UV detector at 254 nm was employed. Results are summarized in Table 1.

TABLE 1

Resolution Using Various CSPs

| Racemate | A | Chiralcel OD[1] | Covalent OD[2] | Whelk-O 1[3] |
|---|---|---|---|---|
| 9-MAC[7] | 1.57[4] | 3.06 | 2.32[6] | 1.12 |
|  | 4.36/6.84[5] | 2.58/7.91 |  | 1.50/1.67 |
| Trogers Base | 1.28 | 1.24 | 1.47[6] | 1.00 |
|  | 2.79/3.57 | 1.30/1.62 |  |  |

TABLE 1-continued

Resolution Using Various CSPs

| Racemate | A | Chiralcel OD[1] | Covalent OD[2] | Whelk-O 1[3] |
|---|---|---|---|---|

[1]Daicel Chemical Industries, Ltd.
[2]E. Yashima et al., J. Chromatogr., (1994) 11–19
[3]Regis Technologies, Inc.
[4]Separation value, α.
[5]k' value for the two enantiomers; see text.
[6]Literature values at a flow rate of 0.5 mL/min.
[7]9-MAC is 2,2,2-trifluoro-1-(9-anthryl)ethanol.

What is claimed is:

1. A chiral stationary phase comprising: a carrier of a refractory inorganic oxide, said carrier covalently bonded via bound surface hydroxyl groups to silicon atoms contained in a spacer agent of formula $(RO)_x Hal_y Si(CH_2)_n NCO$, where R is an alkyl group, Hal is a halogen, x and y are integers such that x+y=3, and n is an integer from 1 up to about 12, where said spacer agent is covalently bonded to a chiral polysaccharide by reaction of its NCO group with an OH group of the polysaccharide.

2. The chiral stationary phase of claim 1 where the refractory inorganic oxide is selected from the group consisting of silica, alumina, titania, zirconia, chromia, boria, silica-alumina, and combinations thereof.

3. The chiral stationary phase of claim 2 where the refractory inorganic oxide is alumina or silica.

4. The chiral stationary phase of claim 3 where the refractory inorganic oxide is silica.

5. The chiral stationary phase of claim 1 where n=2–4.

6. The chiral stationary phase of claim 5 where n=3.

7. The chiral stationary phase of claim 1 where R is an alkyl group having from 1 to 6 carbon atoms.

8. The chiral stationary phase of claim 7 where the alkyl group has 1 or 2 carbon atoms.

9. The chiral stationary phase of claim 1 where the polysaccharide is cellulose.

10. The chiral stationary phase of claim 1 where the polysaccharide is a cellulose carboxylate ester.

11. The chiral stationary phase of claim 1 where the polysaccharide is a cellulose carbamate.

12. The chiral stationary phase of claim 1 where the cellulose carbamate is a cellulose phenyl carbamate.

13. The chiral stationary phase of claim 12 where the cellulose phenyl carbamate is cellulose 3,5-dimethylphenyl carbamate.

14. A chiral stationary phase comprising a carrier, a spacer, and a chiral polysaccharide or derivatized polysaccharide, where said carrier is a refractory inorganic oxide having bound surface hydroxyl groups, where said spacer has one terminus covalently bonded to the bound surface hydroxyl groups of the carrier via O-Si linkages and the other terminus covalently bonded to the hydroxyl groups of the polysaccharide or polysaccharide derivative via NHC(O)O-linkages, the parent of said spacer being an isocyanato alkylene silane of formula $(RO)_x Hal_y (CH_2)_n NCO$, where R is an alkyl group, Hal is a halogen, x and y are integers such that x+y=3, and n is an integer from 1 up to about 12.

15. The chiral stationary phase of claim 14 where the refractory inorganic oxide is selected from the group consisting of silica, alumina, titania, zirconia, chromia, boria, silica-alumina, and combinations thereof.

16. The chiral stationary phase of claim 15 where the refractory inorganic oxide is alumina or silica.

17. The chiral stationary phase of claim 16 where the refractory inorganic oxide is silica.

18. The chiral stationary phase of claim 14 where n=2–4.

19. The chiral stationary phase of claim 18 where n=3.

20. The chiral stationary phase of claim 14 where R is an alkyl group having from 1 to 6 carbon atoms.

21. The chiral stationary phase of claim 20 where the alkyl group has 1 or 2 carbon atoms.

22. The chiral stationary phase of claim 14 where the polysaccharide is cellulose.

23. The chiral stationary phase of claim 14 where the polysaccharide is a cellulose carboxylate ester.

24. The chiral stationary phase of claim 14 where the polysaccharide is a cellulose carbamate.

25. The chiral stationary phase of claim 24 where the cellulose carbamate is a cellulose phenyl carbamate.

26. The chiral stationary phase of claim 25 where the cellulose phenyl carbamate is cellulose 3,5-dimethylphenyl carbamate.

* * * * *

UNITED STATES PATENT AND TRADEMARK OFFICE
CERTIFICATE OF CORRECTION

PATENT NO: 5,811,532
DATED: Sep. 22, 1998
INVENTOR(S): HOUSE

It is certified that error appears in the above-identified patent and that said Letters Patent is hereby corrected as shown below:

In Claim 14, line 15, after "$Hal_y$ and before $(CH_2)_n$," insert ---Si--.

Signed and Sealed this

Twenty-ninth Day of December, 1998

*Attest:*

BRUCE LEHMAN

*Attesting Officer*  *Commissioner of Patents and Trademarks*